US00PP14844P3

(12) United States Plant Patent
Randag

(10) Patent No.: US PP14,844 P3
(45) Date of Patent: Jun. 1, 2004

(54) CALLA LILY PLANT NAMED 'BLACK STAR'

(50) Latin Name: *Zantedeschia sprengeri*
Varietal Denomination: Black Star

(75) Inventor: Cecilius Jan-Jochem Randag, Schagen (NL)

(73) Assignee: Sande BV, CJ 'T (NL)

( * ) Notice: Subject to any disclaimer, the term of this patent is extended or adjusted under 35 U.S.C. 154(b) by 0 days.

(21) Appl. No.: 10/241,892

(22) Filed: Sep. 12, 2002

(65) Prior Publication Data

US 2004/0055064 P1 Mar. 18, 2004

(51) Int. Cl.[7] ..... A01H 5/00

(52) U.S. Cl. ..... Plt./263

(58) Field of Search ..... Plt./263

*Primary Examiner*—Anne Marie Grunberg
*Assistant Examiner*—Susan B. McCormick
(74) *Attorney, Agent, or Firm*—Webb Ziesenheim Logsdon Orkin & Hanson, P.C.

(57) ABSTRACT

'Black Star' is a new variety of calla lily having a flower with a purple/black colored spathe and a purple/black colored spadix and producing 1–4 flowers per tuber. The flower stems are red and about 50 cm in height. The leaves are green with whitish spots and have a leathery texture. On the edge of the leaves there is a red stripe. The petioles have a red to black color.

3 Drawing Sheets

Botanical classification: *Zantedeschia sprengeri.*
Varietal denomination: 'Black Star'.

BACKGROUND OF THE NEW PLANT

The present invention comprises a new and distinct cultivar of calla lily, botanically known as *Zantedeschia sprengeri* and herein after referred to by the cultivar name 'Black Star'.

'Black Star' is a product of a planned breeding program which had the objective of creating Zantedeschia hybrids for cut flower production in a wide range of colors with a large, classic flower shape. The breeding program began in 1989 and the new cultivar is a seedling selected from the cross of a *Zantedeschia sprengeri* variety known as 'Schwarzwalder' female patent (U.S. Plant Pat. No. 11,001), with a *Zantedeschia sprengeri* seedling, male parent. 'Black Star' was orginated in 1998 by the inventor Cecilius Jan-Jochem Randag in 't Zand, The Netherlands as one flowering plant within the progeny of the stated cross.

Table 1 provides a comparison of the new variety to its parents:

TABLE 1

| | Similarities | Differences |
|---|---|---|
| Female Parent | Leaf shape | Darker spathe color |
| | Plant height | Darker peduncle and petiole color |
| | | Dark leaf edge |
| Male parent | Dark leaf edge | Leaf shape |
| | Peduncle color | Flower color |
| | | Plant height |

The first act of asexual reproduction of 'Black Star' by tissue culture was performed by the inventor in August 2000 in 't Zand, The Netherlands. Subsequent asexual reproduction by tissue culture at the same location has demonstrated that the combination of characteristics as herein disclosed for the new cultivar are retained through successive generations of asexual reproduction.

The following traits have been repeatedly observed and determined to be basic characteristics of 'Black Star' which, in combination, distinguish this calla lily as a new and distinct cultivar:

1. Deep purple spathe;
2. Deep purple spadix;
3. Red flower stem;
4. Red edge on the leaves; and
5. Red/black petiole of the leaves.

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

Figure 1:
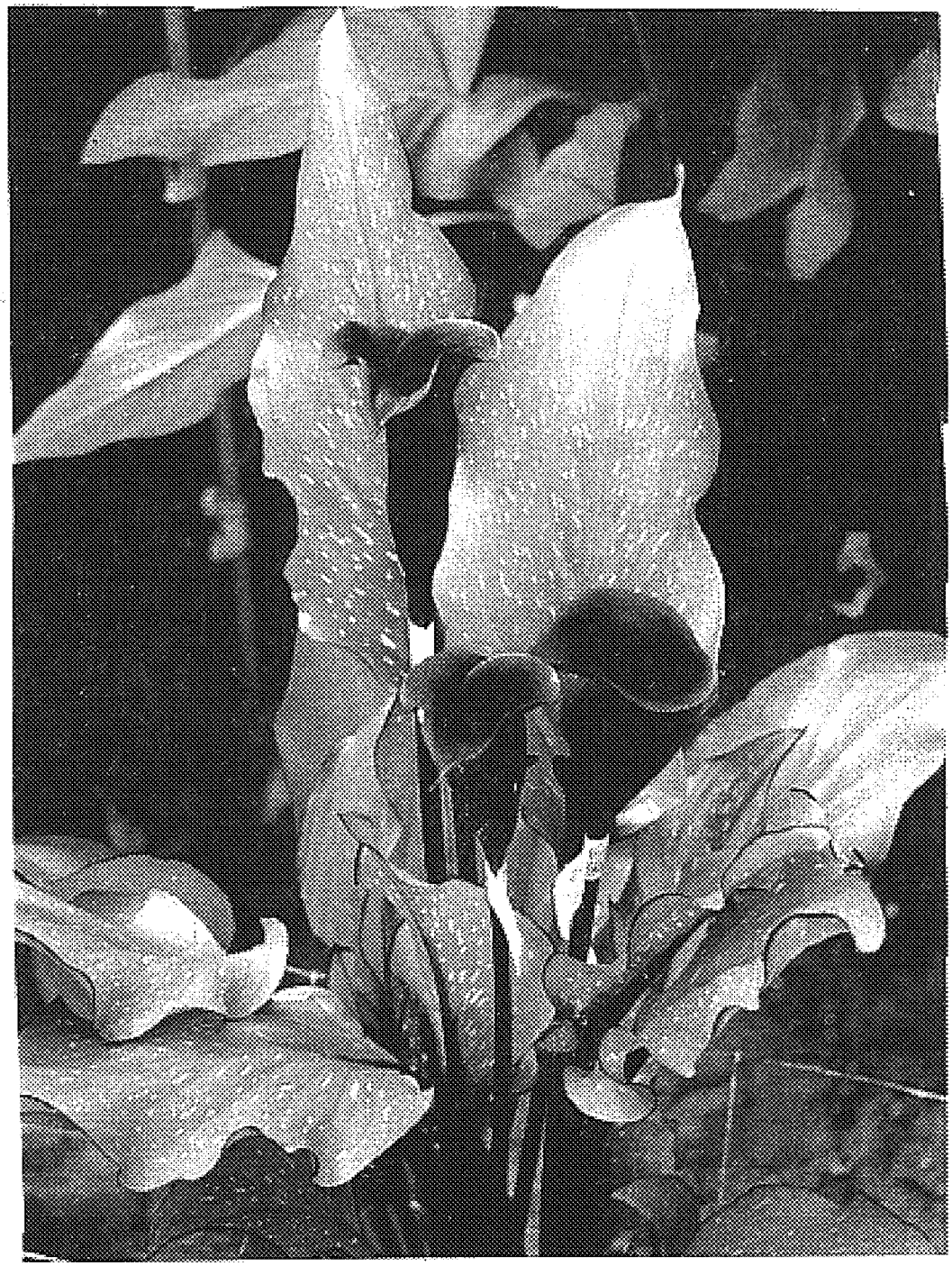
FIG. 1 illustrates the flowers of the new variety.
Figure 2:
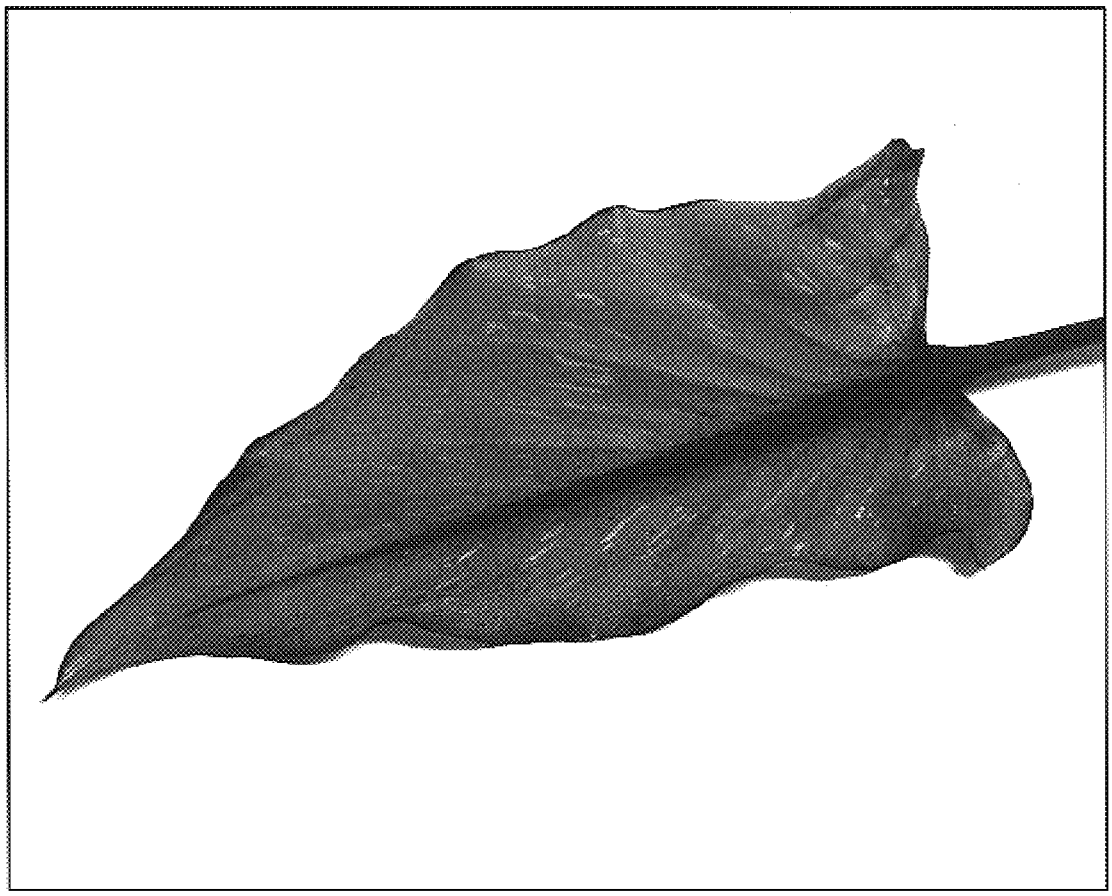
FIG. 2 illustrates the underside of a mature leaf.
Figure 3:
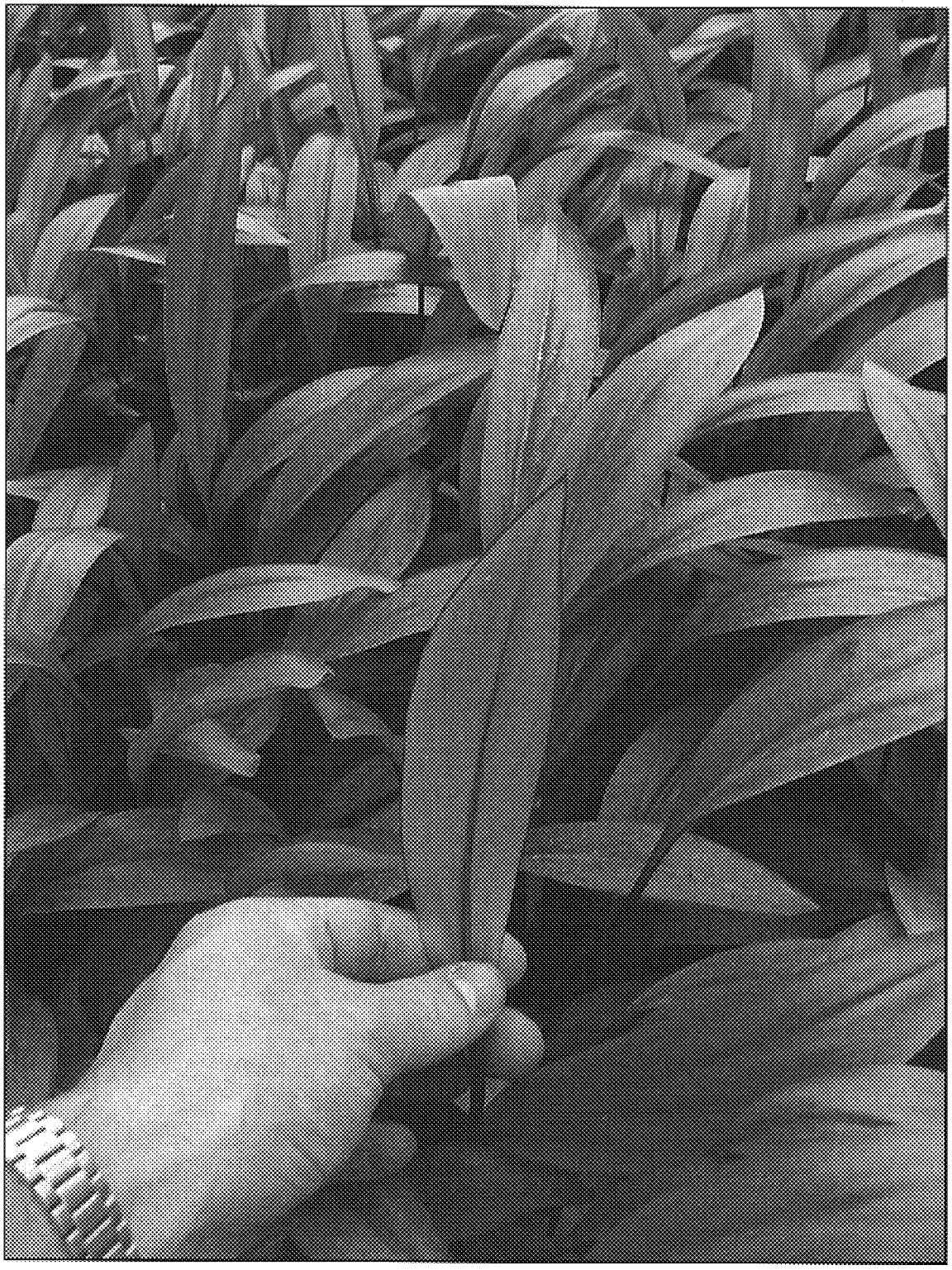
FIG. 3 illustrates the underside of a young leaf.

The following observations, measurements, and comparisons describe plants grown in 't Zand, The Netherlands under greenhouse conditions which approximate those generally used in horticulture practice. The new variety was 3 years old when described. Color references are made to The R.H.S. Colour Chart of The Royal Horticultural Society of London, except where general color terms of ordinary significance are used.

THE PLANT

Size:

*Height of the leaf canopy above the soil.*—50–65 cm.
*Height of top of inflorescence above the soil.*—60–75 cm.

*Diameter.*—30–40 cm.
*Form.*—Erect.

Number of inflorescences per tuber size:
*Length 9–12 cm.*—0–1 inflorescences.
*Length 12–15 cm.*—1–3 inflorescences.
*Length 15–18 cm.*—3–4 inflorescences.

Branches:
*Number.*—Average.
*Color.*—Between 143A and 144A with spots of 53A.

Leaves:
*Size.*—Width: 11–15 cm. Length: 20–30 cm.
*Number per plant.*—4–10.
*Shape.*—Elliptic.
*Color.*—Upper surface: Betwen 137A and 137B. Lower surface: Between 137A and 137B. Speckling: Between 157A and 157C.
*Margin.*—Wavy, having an edge color between 187A and 187B.
*Veins.*—Configuration: Pinnate. Color: Between 144A and 53A.
*Surface quality.*—Leathery.

Petiole:
*Length.*—30–50 cm.
*Color.*—Base is 53A, upper part varies between 53A and 202A.

Roots:
*Color.*—White.
*Branching.*—Average; similar to other Zantedeschia varieties.

THE FLOWER

Spathe:
*Size.*—Length: 8–10 cm. Width: 5–7 cm.
*Color.*—Upper surface: Varies between 187A and 202A. Lower surface: Varies between 187A and 202A.
*Veins.*—Color: Varies between 187A and 202A.
*Shape.*—Cupped.

Spadix:
*Size.*—Length: 20–45 mm. Diameter: 3–7 mm.
*Color.*—187A.
*Position relative to spathe.*—Upright.

Peduncle:
*Size.*—Length: 50–65 cm. Diameter: 8–10 mm.
*Color.*—Varies between 53A and 202A.

Reproductive organs:
*Location of female organs.*—Basal position of the spadix.
*Location of male organs.*—Upper position of the spadix.
*Stemens.*—Presence: Not visible before pollen release. Number: More than 50. Pollen: Amount: Similar to 'Schwarzwalder', less than 'Pot of Gold'. Color: 155A to 155B. Anther: Shape: Wire-like. Length: Less than 1 mm. Color: Between 155A and 155B. Filament: Length: Less than 1 mm. Color: Between 155A and 155B.
*Pistil.*—Number: 20–40. Length beyond perianth: About 1 mm. Stigma: Shape: Round. Size: Less than 1 mm. Style: Length: Less than 1 mm. Color: 187A. Ovaries: Texture: Smooth. Length: Between 1 to 10 mm. Width: Between 1 to 10 mm. Color: Top: 187A. Bottom: 193B.
*Seeds.*—Length: 4–7 mm. Width: 3–6 mm. Color: Between 187A and 187B. Amount: Between 1 to 25.

GENERAL

Flowering: Tubers planted in a greenhouse in The Netherlands in February produce flowers in April. Tubers planted outdoors in The Netherlands in May produce flowers in July.
Lastingness: About three weeks on the plant.
Fragrance: None.
Disease/pest resistance: No unusual susceptibility to diseases or pests has been noted to date.
Winter hardiness: None.
Drought/heat tolerance: None.

I claim:

1. A new and distinct calla lily plant named 'Black Star' as herein described and illustrated.

* * * * *